(12) United States Patent
Porges et al.

(10) Patent No.: US 6,675,031 B1
(45) Date of Patent: Jan. 6, 2004

(54) METHOD AND CIRCUIT FOR INDICATING QUALITY AND ACCURACY OF PHYSIOLOGICAL MEASUREMENTS

(75) Inventors: Charles Porges, Orinda, CA (US); Clark Baker, Castro Valley, CA (US); Thomas J. Yorkey, San Ramon, CA (US); Michael Bernstein, San Ramon, CA (US); Paul Mannheimer, Danville, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/545,170

(22) Filed: Apr. 6, 2000

Related U.S. Application Data

(60) Provisional application No. 60/129,170, filed on Apr. 14, 1999.

(51) Int. Cl.[7] .................................................. A61B 5/00
(52) U.S. Cl. ........................ 600/322; 600/330; 600/331
(58) Field of Search .............................. 600/309–310, 600/316, 326, 322–324, 330, 334, 331

(56) References Cited

U.S. PATENT DOCUMENTS

| | | | | | |
|---|---|---|---|---|---|
| 4,653,498 A | * | 3/1987 | New, Jr. et al. | ............. | 600/324 |
| 4,858,615 A | * | 8/1989 | Meinema | ................... | 600/481 |
| 4,942,877 A | | 7/1990 | Sakai et al. | | |
| 4,974,591 A | * | 12/1990 | Awazu et al. | ............... | 600/344 |
| 5,190,038 A | * | 3/1993 | Polson et al. | ............... | 600/330 |
| 5,782,758 A | * | 7/1998 | Ausec et al. | ............... | 600/336 |
| 5,846,190 A | * | 12/1998 | Woehrle | ..................... | 600/330 |
| 5,987,343 A | * | 11/1999 | Kinast | ........................ | 600/323 |
| 6,104,938 A | * | 8/2000 | Huiku et al. | ............... | 600/322 |

FOREIGN PATENT DOCUMENTS

| | | |
|---|---|---|
| EP | 0 221 357 A2 | 5/1987 |
| EP | 0 571 225 A2 A3 | 11/1993 |
| WO | WO 00/61000 A1 | 10/2000 |

\* cited by examiner

*Primary Examiner*—Eric F. Winakur
*Assistant Examiner*—Matthew Kremer
(74) *Attorney, Agent, or Firm*—Townsend & Townsend & Crew LLP

(57) ABSTRACT

Sensors and monitors for a physiological monitoring system having capability to indicate an accuracy of an estimated physiological condition. The sensor senses at least one physiological characteristic of a patient and is connectable to a monitor that estimates the physiological condition from signals detected by the sensor. The sensor includes a detector for detecting the signals from the patient which are indicative of the physiological characteristic. The sensor is associated with a memory configured to store data that defines at least one sensor signal specification boundary for the detected signals. The boundary is indicative of a quality of the signals and an accuracy of the physiological characteristic estimated from the signals by the monitor. The sensor further includes means for providing access to the memory to allow transmission of the data that defines the at least one sensor boundary to the monitor.

20 Claims, 11 Drawing Sheets

METHOD AND CIRCUIT FOR INDICATING QUALITY AND ACCURACY OF PHYSIOLOGICAL MEASUREMENTS

This application claims the benefit of U.S. Provisional Application Ser. No. 60/129,170, filed Apr. 14, 1999, which is incorporated herein by reference.

BACKGROUND OF THE INVENTION

The present invention relates to physiological monitoring instruments and, in particular, monitors and sensors that include mechanisms for indicating a quality of detected signals and accuracy or confidence level of physiological measurements estimated from the signals.

Typically, for physiological monitoring instruments that include a monitor and a patient sensor, the monitor is unable to accurately determine a quality of a signal obtained from the sensor. The invention will be explained by reference to a preferred embodiment concerning pulse oximeter monitors and pulse oximetry sensors, but it should be realized the invention is applicable to any generalized patient monitor and associated patient sensor. The invention provides a way of more accurately determining a quality of a signal detected by a sensor; a way of determining a relative accuracy of a physiological characteristic derived or calculated from the signal; and a way of delineating a transition boundary between a normal signal for the sensor being used in its normal application, and a signal considered to be abnormal for the sensor being used, to allow a monitor to determine if the sensor is being misapplied.

Pulse oximetry is typically used to measure various blood flow characteristics including, but not limited to, the blood oxygen saturation of hemoglobin in arterial blood and the heartbeat of a patient. Measurement of these characteristics has been accomplished by the use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical signal is a familiar plethysmographic waveform due to the cycling light attenuation.

The light passed through the tissue is typically selected to be of two or more wavelengths that are absorbed by the blood in an amount related to the amount of blood constituent present in the blood. The amount of transmitted light that passes through the tissue varies in accordance with the changing amount of blood constituent in the tissue and the related light absorption.

To estimate arterial blood oxygen saturation of a patient, conventional two-wavelength pulse oximeters emit light from two light emitting diodes (LEDs) into a pulsatile tissue bed and collect the transmitted light with a photodiode (or photo-detector) positioned on an opposite surface (i.e., for transmission pulse oximetry) or an adjacent surface (i.e., for reflectance pulse oximetry). The LEDs and photo-detector are typically housed in a reusable or disposable oximeter sensor that couples to a pulse oximeter electronics and display unit. One of the two LEDs' primary wavelength is selected at a point in the electromagnetic spectrum where the absorption of oxyhemoglobin ($HbO_2$) differs from the absorption of reduced hemoglobin (Hb). The second of the two LEDs' wavelength is selected at a different point in the spectrum where the absorption of Hb and $HbO_2$ differs from those at the first wavelength. Commercial pulse oximeters typically utilize one wavelength in the near red part of the visible spectrum near 660 nanometers (nm) and one in the near infrared (IR) part of the spectrum in the range of 880–940 nm.

Oxygen saturation can be estimated using various techniques. In one common technique, first and second photo-current signals generated by the photo-detector from red and infrared light are conditioned and processed to determine AC and DC signal components and a modulation ratio of the red to infrared signals. This modulation ratio has been observed to correlate well to arterial oxygen saturation. Pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios. The estimation of oxygen saturation using modulation ratio is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. All three patents are assigned to the assignee of the present invention and incorporated herein by reference.

The accuracy of the estimates of the blood flow characteristics depends on a number of factors. For example, the light absorption characteristics typically vary from patient to patient depending on their physiology. Moreover, the absorption characteristics vary depending on the location (e.g., the foot, finger, ear, and so on) where the sensor is applied. Further, the light absorption characteristics vary depending on the design or model of the sensor. Also, the light absorption characteristics of any single sensor design vary from sensor to sensor (e.g., due to different characteristics of the light sources or photo-detector, or both). The clinician applying the sensor correctly or incorrectly may also have a large impact in the results, for example, by loosely or firmly applying the sensor or by applying the sensor to a body part which is inappropriate for the particular sensor design being used.

Some oximeters "qualify" measurements before displaying them on the monitor. One conventional technique processes (i.e., filters) the measured plethysmographic waveform and performs tests to detect and reject measurements perceived corrupted and inaccurate. Since oximeters are typically designed to be used with a wide variety of sensors having widely differing performance characteristics, the monitor signal "qualification" algorithms are necessarily crude, and often result in only superficial indications of signal quality, signal reliability, and ultimately a confidence level in a patient physiological characteristic estimated or calculated from the signal. In many instances, the monitor simply discards data associated with low quality signals, but otherwise gives no indication to a healthcare giver as to whether any physiological characteristic displayed on a monitor is highly reliable or not. Hence, the signal quality measurements obtained from such crude algorithms are relatively poor and convey little useful information to a caregiver.

SUMMARY OF THE INVENTION

Accordingly, it is an object of the present invention to provide a patient monitor and sensor which includes means for accurately detecting a quality of a signal detected by the sensor.

Another object of the invention is to provide a monitor and sensor which includes means for accurately determining a quality of a physical characteristic estimated from a signal obtained by a sensor.

A further object of the invention is to provide a monitor and sensor which includes means for detecting a transition between a signal regime considered normal for the sensor in its usual application, and a signal regime considered to be abnormal.

These and others objects of the invention are achieved by the use of a set of one or more signal specification boundaries. Each boundary defines a region of a signal quality diagram and corresponds to a different level of quality in the detected signals and accuracy or confidence level of physiological characteristic estimated from the detected signals. Boundaries can also be defined for and associated with different sensor types and monitor types. The boundaries are typically stored in a memory and accessed when required.

An embodiment of the invention provides a sensor for sensing at least one physiological characteristic of a patient. The sensor is connectable to a monitor that estimates a physiological condition from signals detected by the sensor. The sensor includes a detector for detecting the signals from the patient which are indicative of the physiological characteristic. The sensor is associated with a memory configured to store data that defines at least one sensor signal specification boundary for the detected signals. The boundary is indicative of a quality of the signals and an accuracy of the physiological characteristic estimated from the signals by the monitor. The sensor further includes means for providing access to the memory to allow transmission of the data that defines the at least one sensor boundary to the monitor.

In an embodiment, the boundary is indicative of a transition between a signal regime considered normal for the sensor in its usual application, and a signal regime considered to be abnormal. The normal regime can be one in which the sensor is likely to be properly applied to the patient and the abnormal regime can be one in which the sensor may have partially or entirely come off the patient.

Another embodiment of the invention provides a monitor for providing an indication of an accuracy of an estimated physiological condition of a patient. The monitor is connectable to a sensor that detects signals indicative of at least one physiological characteristic of the patient. The monitor includes at least one receiving circuit and at least one processing circuit. The receiving circuit is configured to receive the signals indicative of the at least one physiological characteristic and data defining at least one sensor signal specification boundary for the detected signals. The processing circuit is configured to estimate the physiological condition of the patient based on the received signals, compare the received signals against the at least one sensor boundary, and generate the indication of the accuracy of the estimated physiological condition. The monitor further includes means for providing the indication of the accuracy of the estimated physiological condition to a user of the monitor.

Yet another embodiment of the invention provides a pulse oximetry system that includes the sensor described above and a pulse oximetry monitor. The monitor has means to determine whether the signals are within a normal regime or an abnormal regime. The system further includes means for informing a user of the system as to whether the signal is normal or abnormal.

The foregoing, together with other aspects of this invention, will become more apparent when referring to the following specification, claims, and accompanying drawings.

DESCRIPTION OF THE SPECIFIC EMBODIMENTS

The invention is applicable to measurement (or estimation) of oxygen saturation of hemoglobin in arterial blood and patient heart rate. The invention will be described in detail with respect to an embodiment for pulse oximetry, but it needs to be realized that the invention has applicability to alternate patient monitoring characteristics, such as ECG, blood pressure, temperature, etc., and is not to be limited to only for use with oximetry or pulse oximetry.

Figure 1:
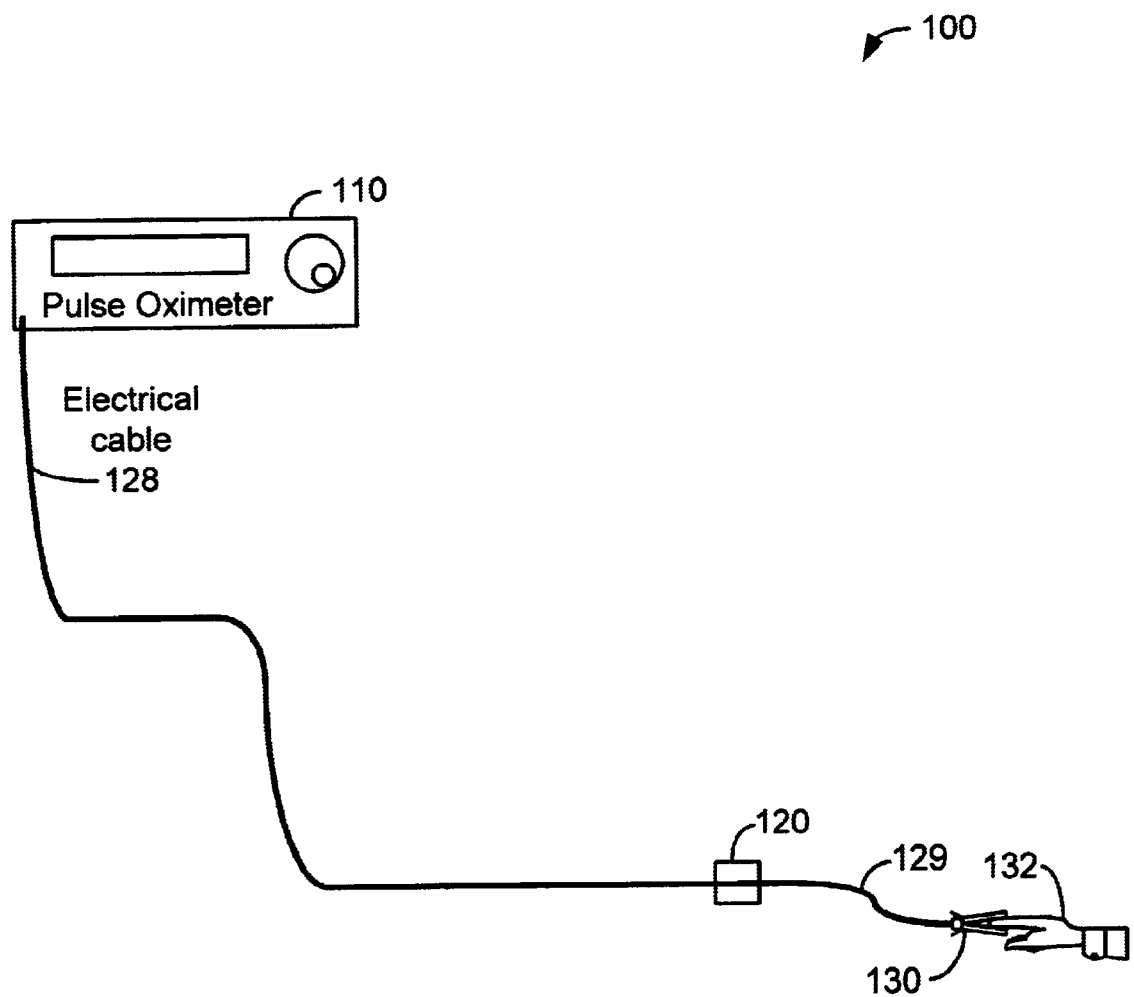
FIG. 1 shows a simplified block diagram of an embodiment of a pulse oximeter system.

FIG. 1 shows a simplified block diagram of an embodiment of a pulse oximeter system 100. System 100 includes a pulse oximeter (or monitor) 110 that couples via an electrical cable 128 to a sensor 130 that is applied to a patient 132. Sensor 130 includes a sensor cable 129 and a connector plug 120. The sensor further has first and second light sources (e.g., LEDs) and a photo-detector along with suitable components to couple these electro-optical components to the electrical cable 128.

As noted above, oxygen saturation can be estimated using various techniques. In one common technique, the optical signals are received by the photo-detector, and conditioned and processed by the oximeter to generate AC and DC components. These components are then used to compute a modulation ratio of the red to infrared signals. The computed modulation ratio is then indexed against a table to retrieve a saturation estimate corresponding to that modulation ratio.

Figure 2A:
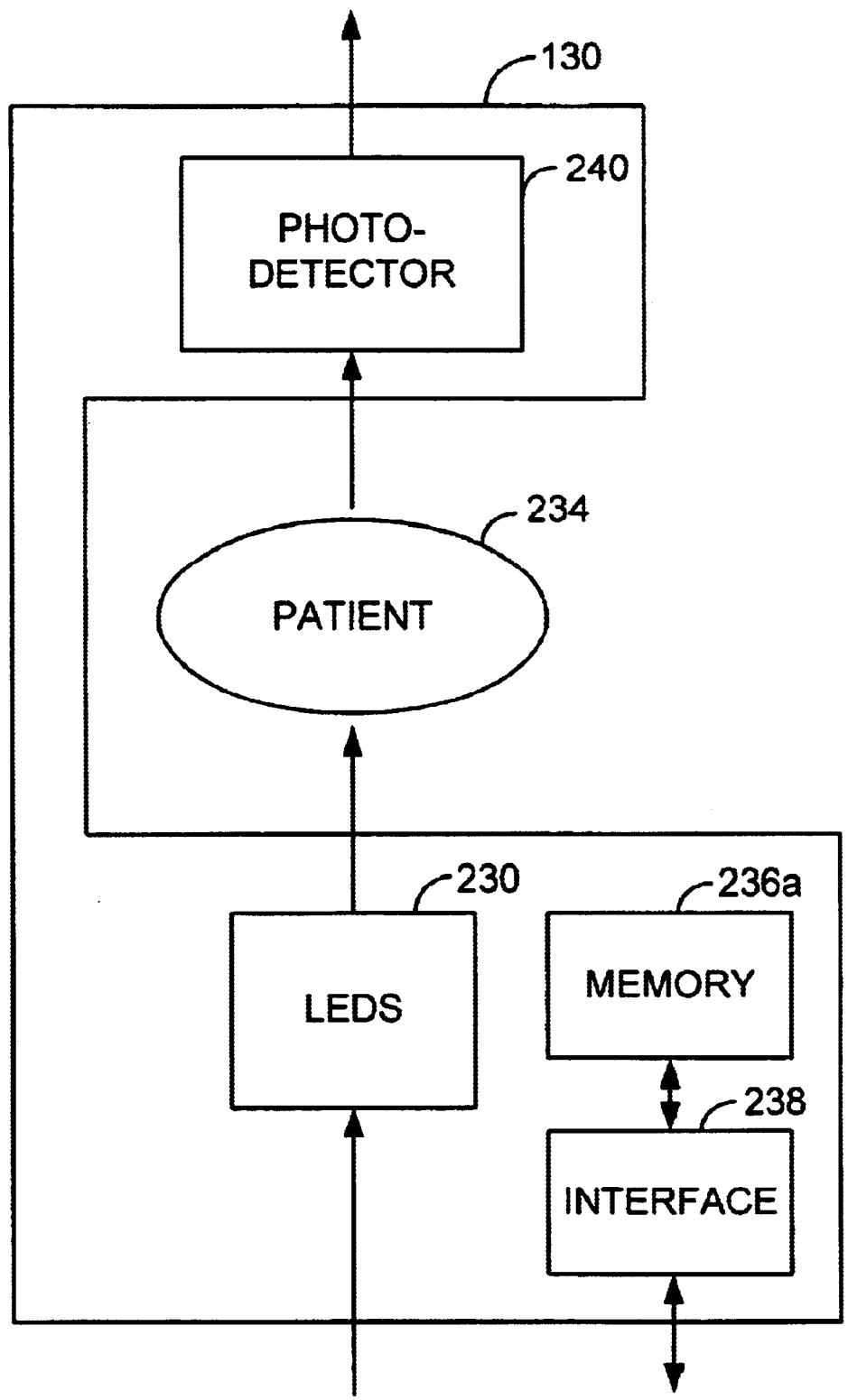
FIG. 2A shows a diagram of a specific embodiment of a sensor.

FIG. 2A shows a diagram of a specific embodiment of sensor 130. Sensor 130 includes two or more LEDs 230 and a photodetector 240. Sensor 130 may optionally include a memory 236a and an interface 238. LEDs 230 receive drive signals that (i.e., alternately) activate the LEDs. When activated, the light from LEDs 230 passes into a patient's tissues 234. After being transmitted through or reflected from the tissues, the light is received by photo-detector 240. Photo-detector 240 converts the received light into a photocurrent signal, which is then provided to the subsequent signal-processing unit.

The sensor memory stores data representative of at least one sensor signal specification boundary and provides the sensor boundary when requested. Interface circuit 238 provides signal conditioning, and can also provide other functions. Through interface circuit 238, data is transferred to and from the sensor memory. Memory 236a and interface circuit 238 can be integrated within one integrated circuit for reduced size and cost.

The memory associated with the sensor can be physically located in a variety of places. First, it can be located on the body of the sensor, in a vicinity of the photodetector, LEDs, or other sensor components. Or, the memory can be in the sensor cable 129 or the connector plug 120, or in an adapter module that connects to a front of an oximeter, to an oximeter cable, or to a sensor plug or cable.

Figure 2B:
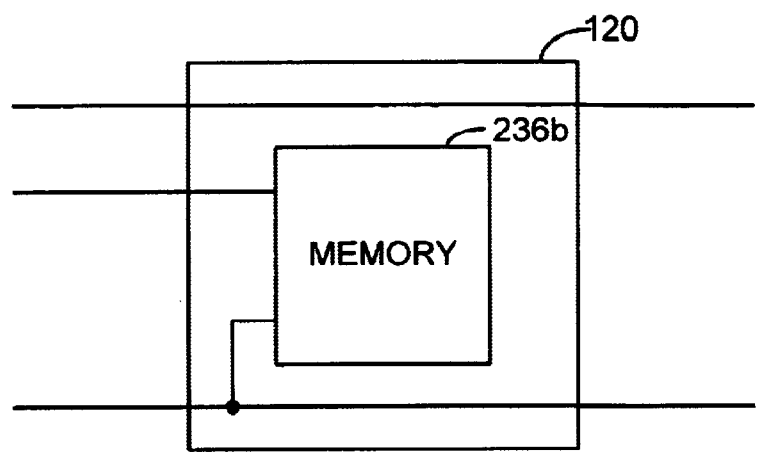
FIGS. 2B and 2C show diagrams of specific embodiments in which a memory is located within the sensor plug and within the sensor cable, respectively.

FIG. 2B shows a diagram of a specific embodiment in which a memory 236b is located within the connector plug 120. Memory 236b couples to and interfaces with external circuitry through some or all signal lines provided to the sensor plug.

Figure 2C:
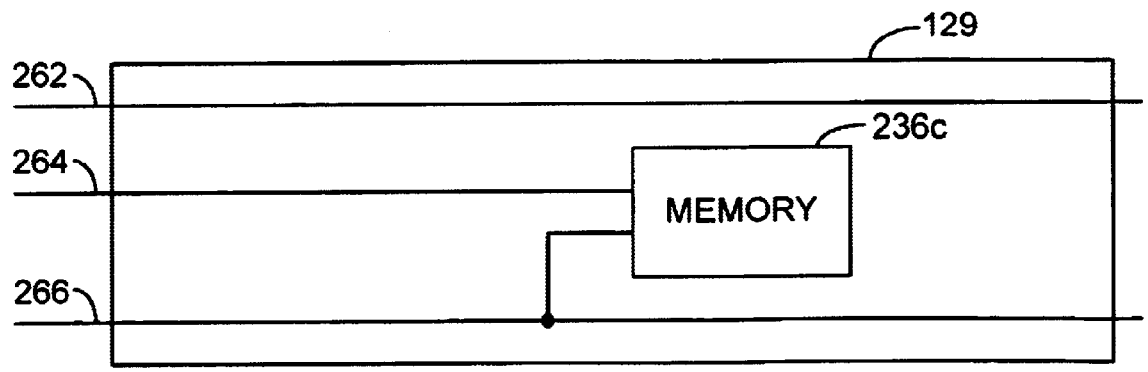

FIG. 2C shows a diagram of a specific embodiment in which a memory 236c is located within the sensor cable 129. Again, memory 236c couples to and interfaces with external circuitry through a set of signal lines.

The memory 236 can be implemented as a random access memory (RAM), a FLASH memory, a programmable read only memory (PROM), an erasable PROM (EPROM), an electrically erasable PROM (EEPROM), a write once memory, or other memory technologies capable of write and read operations. In a specific embodiment, to preserve the data stored in the memory and prevent accidental erasure, the sensor memory can be written only once. This memory characteristic also prevents erasure of the data during sensor operation. A specific example of a memory device that can be written only once is a 2-wire EPROM device available from Dallas Semiconductor Corp.

Figure 2D:
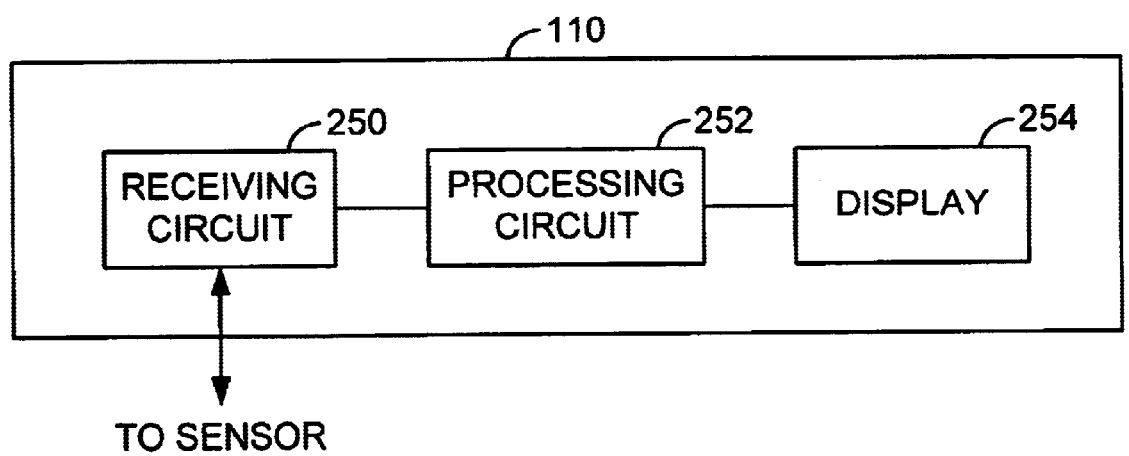
FIG. 2D shows a diagram of a specific embodiment of a monitor.

FIG. 2D shows a diagram of a specific embodiment of monitor 110. A receiving circuit 250 couples to the sensor and the memory associated with the sensor for receiving signals detected by the sensor and data from the sensor memory. The receiving circuit 250 couples to a processing circuit 252 that processes the received signals to generate an estimate of a physiological characteristic. The processing circuit 252 can further generate an indication of the quality of the received signal and an indication of the accuracy of the estimated physiological characteristic. The estimated physiological characteristic and associated indications are provided to a display unit 254 for display to a user of the monitor.

Figure 3:
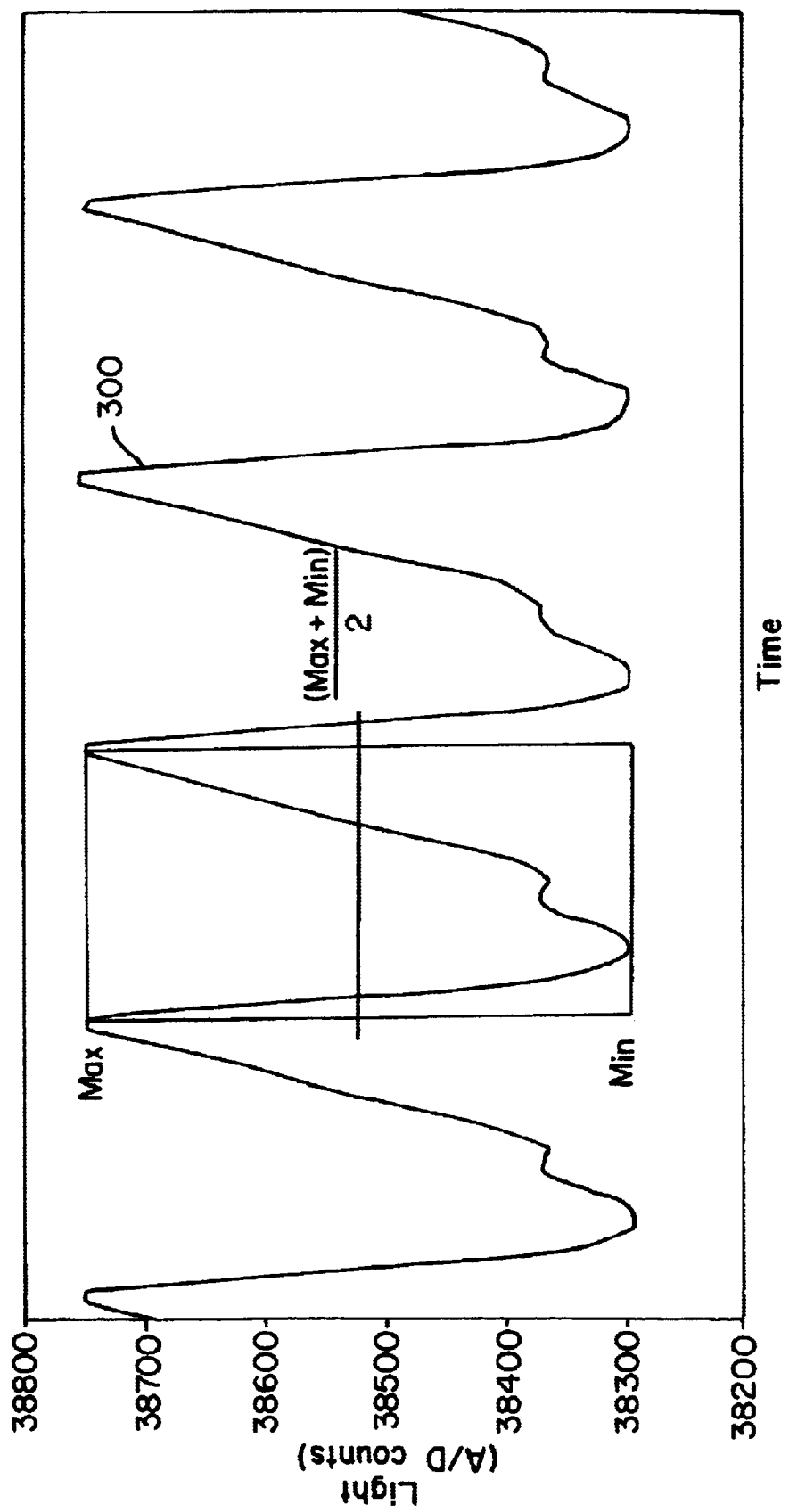
FIG. 3 shows a diagram of a simplified optical waveform detected by the sensor.

FIG. 3 shows a diagram of a simplified optical waveform 300 detected by a sensor (e.g., sensor 130). Optical waveform 300 in FIG. 3 can represent the detected optical signal for either the red or infrared LED. As shown in FIG. 3, optical waveform 300 includes a periodic pattern that generally corresponds to a patient's heartbeat. For arrhythmia patient, the waveform may be aperiodic. Waveform 300 includes a series of peaks having a maximum value (Max) and a series of valleys having a minimum value (Min). The following quantities are defined:

$$AC = \text{Max} - \text{Min}; \quad \text{Eq. (1)}$$

$$DC = \frac{(\text{Max} - \text{Min})}{2}; \quad \text{Eq. (2)}$$

$$\text{Modulation percentage } (Mod \%) = 100 \cdot \left(\frac{AC}{DC}\right); \text{ and} \quad \text{Eq. (3)}$$

$$nAv \text{ (nanoAmperes virtual)} = \frac{DC}{\text{Instrument gain}} \cdot \frac{50 \text{ mA}}{\text{actual LED drive current in mA}} \quad \text{Eq. (4)}$$

where Instrument gain is a gain value that is specific to the combination of the pulse oximeter and a particular sensor that is used during the detection of the pulses in waveform 300. Nanoamperes virtual "normalizes" the signal to a 50 mA LED drive. Many oximeters contain servo systems which adjust LED drive intensity to be optimal for a particular set of monitoring conditions. By normalizing signal levels to a standard assumed LED drive level, it is possible to derive a measure of signal strength which is dependent primarily on the sensor and patient, and not on particular drive level which the instrument has selected.

The modulation ratio of the red to infrared signals, sometimes referred to as the "ratio of ratios" (Ratrat), can be approximated as:

$$Ratrat \cong \frac{\left(\frac{AC\_Red}{DC\_Red}\right)}{\left(\frac{AC\_IR}{DC\_IR}\right)}; \quad \text{Eq. (5)}$$

where AC_Red and DC_Red are the respective AC and DC components of the red LED, and AC_IR and DC_IR are the respective AC and DC components of the infrared LED. Oxygenation derived from Ratrat using equation (5) is sufficiently accurate for many applications when the condition (AC<<DC) is satisfied. Particularly, the approximation error is small when both AC terms in equation (5) are less than ten percent of the related DC terms (i.e., both red and infrared modulations are less than 10%).

As stated above, oxygen saturation is related to Ratrat. The relationship between Ratrat and oxygen saturation is typically plotted as a curve (i.e., saturation versus Ratrat) and stored as a table in the memory within the oximeter. Subsequently, a calculated Ratrat is used to index the table to retrieve an entry in the table for the oxygen saturation estimate corresponding to that Ratrat. The estimation of oxygen saturation using Ratrat is further described in U.S. Pat. Nos. 4,911,167, 5,645,059, and 5,853,364.

Generally, the Red terms are measured in the red part of the optical spectrum using the red LED, and the IR terms are measured in the infrared part of the optical spectrum using the infrared LED. The AC terms are generated by the blood pressure pulse and are somewhat related to "perfusion." The DC terms are (inversely) related to the "opacity" (or darkness) of the patient being monitored and are somewhat related to "translucence." Generally, the four terms in equation (5) arc independent of each other. However, empirical studies suggest that the two DC terms are somewhat correlated (i.e., not wildly divergent), and patients who are "opaque" tend to be opaque in both the red and infrared parts of the spectrum.

It has been determined that the magnitudes of the DC and AC components influence the accuracy of the saturation estimates and these magnitudes depend on the sensor design being used, the specifications of components used in the sensor, and how the sensor has been applied to the patient. The invention advantageously utilizes this knowledge to provide an oximeter system capable of providing indications of the accuracy and reliability of the saturation estimates. Additional features are provided by the invention based on the analysis of the measured DC and AC components, as described below.

Figure 4:
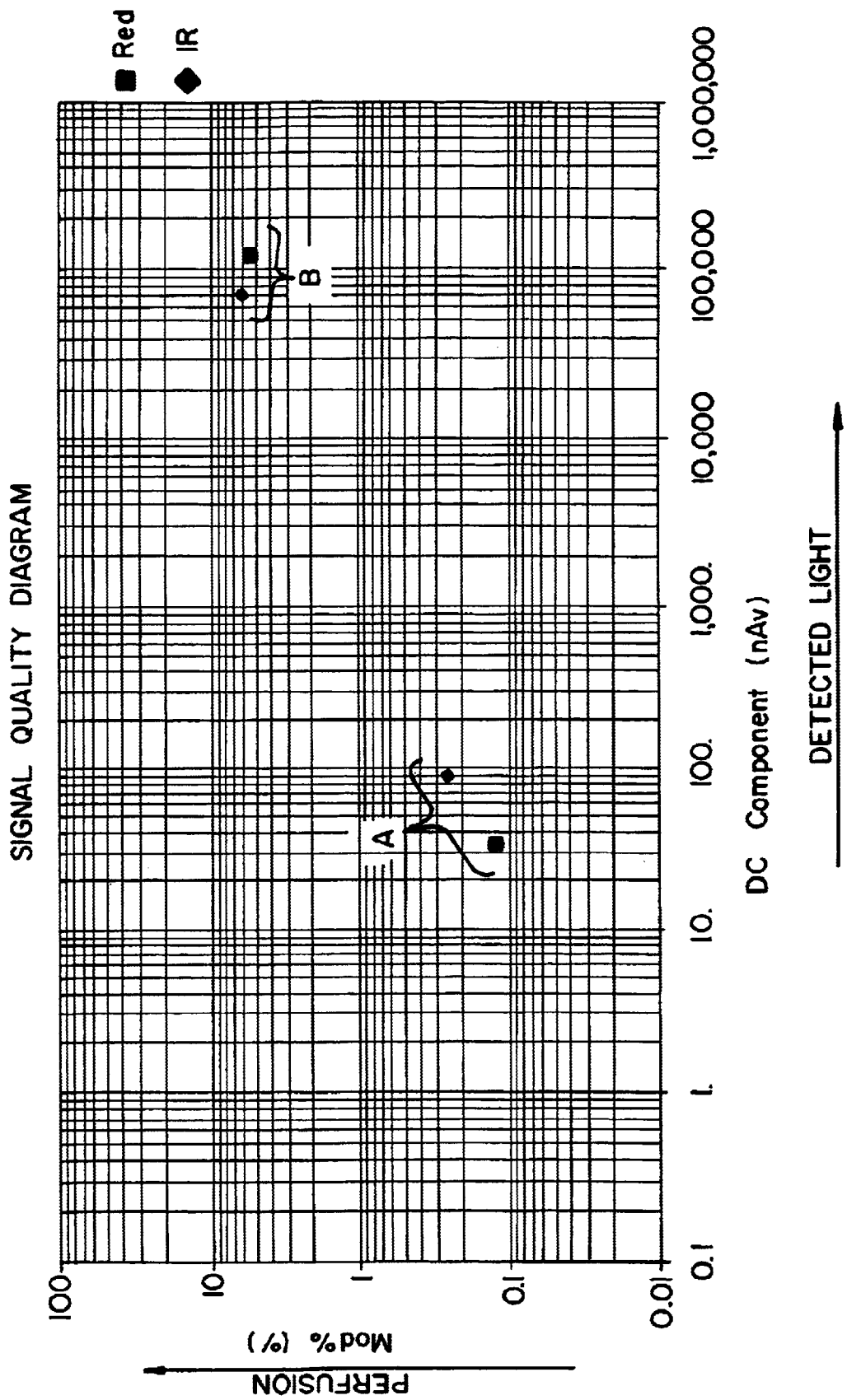
FIG. 4 shows a signal quality diagram that includes data of the measured DC and AC components.

FIG. 4 shows a signal quality diagram that includes data of the measured DC and AC components. The vertical axis of the signal quality diagram corresponds to the modulation percentage (Mod %) which is calculated as shown in equation (3) for each of the red and infrared signals. The horizontal axis corresponds to the DC component and is in units of virtual nano Amperes (nAv) and is given by equation (4). As shown in FIG. 4, both vertical and horizontal axes are plotted on a logarithmic scale.

As noted above, the detected optical waveform includes an AC component and a DC component. The DC component is plotted on the horizontal axis and the ratio of AC to DC is expressed as a percentage (e.g., Mod %) and plotted on the vertical axis. Since two different optical signals are measured (i.e., for the red and infrared wavelengths), two points are generated and plotted on the signal quality diagram to uniquely identify the AC and DC components of both the red and infrared optical signals. In FIG. 4, the data points corresponding to the red wavelength are identified by a square and the data points corresponding to the infrared wavelength are identified by a diamond.

FIG. 4 shows the relative positions of two data points associated with two patients on the signal quality diagram. For a (stable) patient and over a short duration (i.e., of few pulses), all four Ratrat constituents (Red AC, DC; and Infrared AC, DC) remain approximately constant. The data points for patient A indicate a patient with low light levels (i.e., low DC component values) and low modulation (i.e., low Mod %). These data points could correspond to data from, for example, a chubby, dark-skinned neonate who has poor perfusion, or a reflectance sensor applied to a poorly perfused site (i.e., on the foot). Conversely, the data points for patient B indicate a very translucent patient with good perfusion that results in high light levels and high modulation.

The pair of data points for each patient, one data point for red wavelength and one for infrared wavelength, defines the patient's current (Ratrat) conditions. Equivalently, the pair of data points describes the oximeter's "operating point," when the oximeter is monitoring that patient. For a particular patient, the pair of data points can be used to estimate the patient's saturation using equation (5) and a table for saturation versus Ratrat. For example, the Ratrat for patient A is approximately $0.12/0.25$ or 0.48. For a typical oximeter, this Ratrat corresponds to a saturation of approximately 100%. The Ratrat for patient B is approximately $6/7$ or 0.86, which corresponds to a saturation of approximately 85%.

In an embodiment, for each particular combination of oximeter model and sensor model, data points are collected for numerous "patients." These data points can be collected under a controlled test environment where true oxygen saturation is known, and an accuracy of the saturation estimated from the red and infrared signals can be determined. Based on the collected data, the diagram can be partitioned into regions corresponding to different levels of quality and accuracy in the saturation estimate. The regions also indicate a quality of the detected signals. Each region is defined by a signal boundary.

The signal boundaries are dependent on many factors such as the monitor type, sensor type, specifications of components in the sensor (e.g., wavelength, LED characteristics), and other factors. In an embodiment, sensor specific boundaries are stored in the sensor memory or other locations associated with the sensor.

Figure 5:
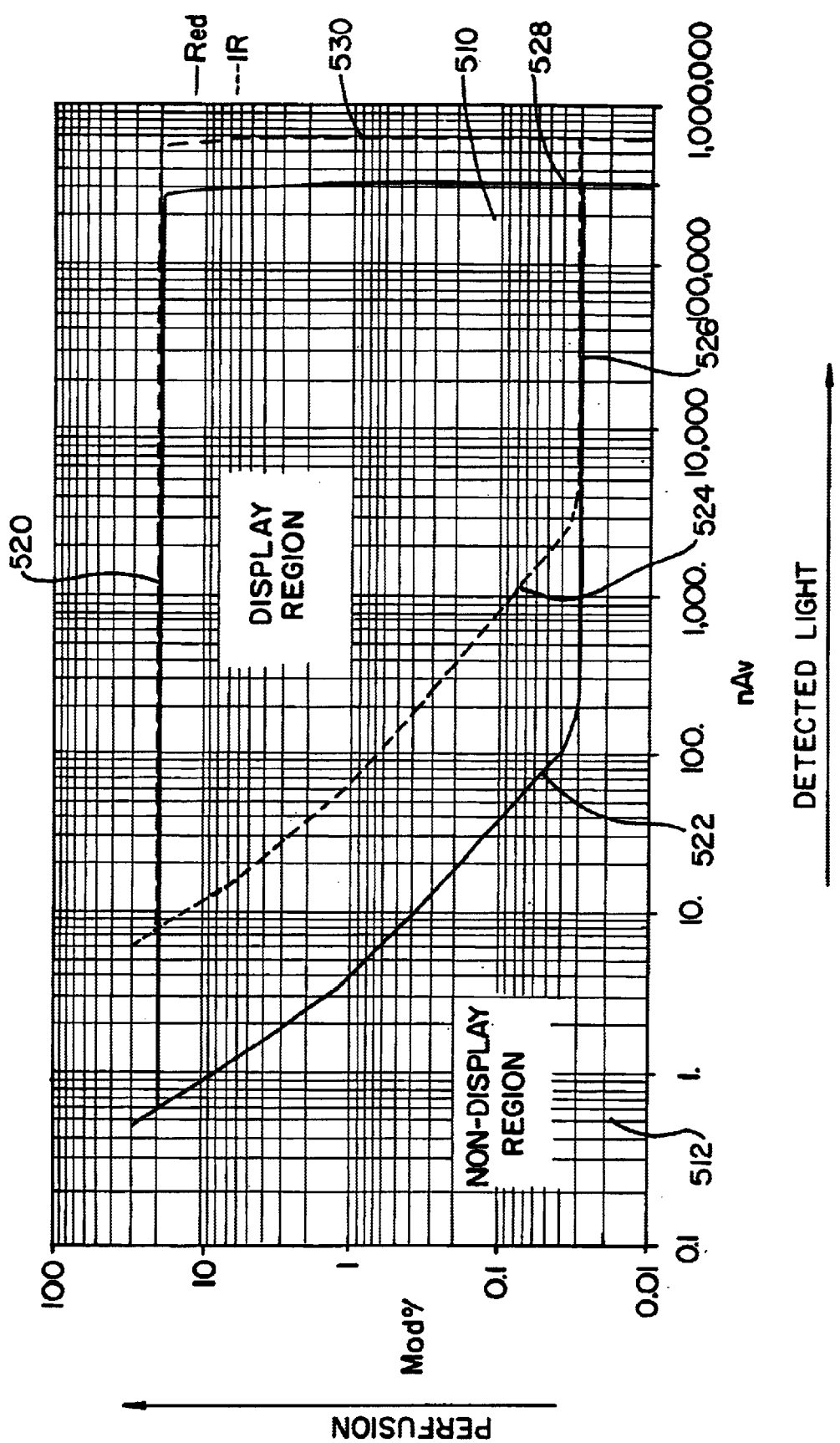
FIG. 5 shows a signal quality diagram having defined regions corresponding to different confidence levels in the saturation estimate.

FIG. 5 shows a sensor signal quality diagram having defined regions corresponding to different confidence levels in the saturation estimate. A display region 510 defines a portion of the signal quality diagram associated with saturation estimates that satisfy a predetermined quality and accuracy level and merit posting (or displaying) on the monitor. Display region 510 includes the set of "patient conditions" resulting in sufficiently accurate saturation estimates for a particular application. Accordingly, when the data points fall within display region 510, the saturation estimate (which is derived from the data points) is posted. Conversely, when the data points fall outside display region 510 into a non-display region 512, the saturation estimate corresponding to these data points is not posted on the oximeter display. Non-display region 512 lies outside, and generally surrounds, display region 510.

The DC signal corresponding to the red LED is generally "weaker" than the detected signal from the infrared LED. Since this characteristic is known a priori, the oximeter can be designed to account for this difference. In one implementation, the red LED is associated with a first display region and the infrared LED is associated with a second display region. For example, referring to FIG. 5, the red display region is defined by lines 520, 522, 526, and 528, and the infrared display region is defined by lines 520, 524, 526, and 530. Since the red signals are generally weaker than the infrared signal, the boundary of the red display region tends to be closer to the lower left corner of the signal quality diagram.

The display region may be dependent on numerous operating conditions. For example, ambient light typically adds to the detected optical signals (i.e., increases the DC components) and thus may alter the display region. In this case, the display region could be adjusted to account for the perturbation of the signal caused by the (or distortion introduced by) ambient light.

Figure 6:
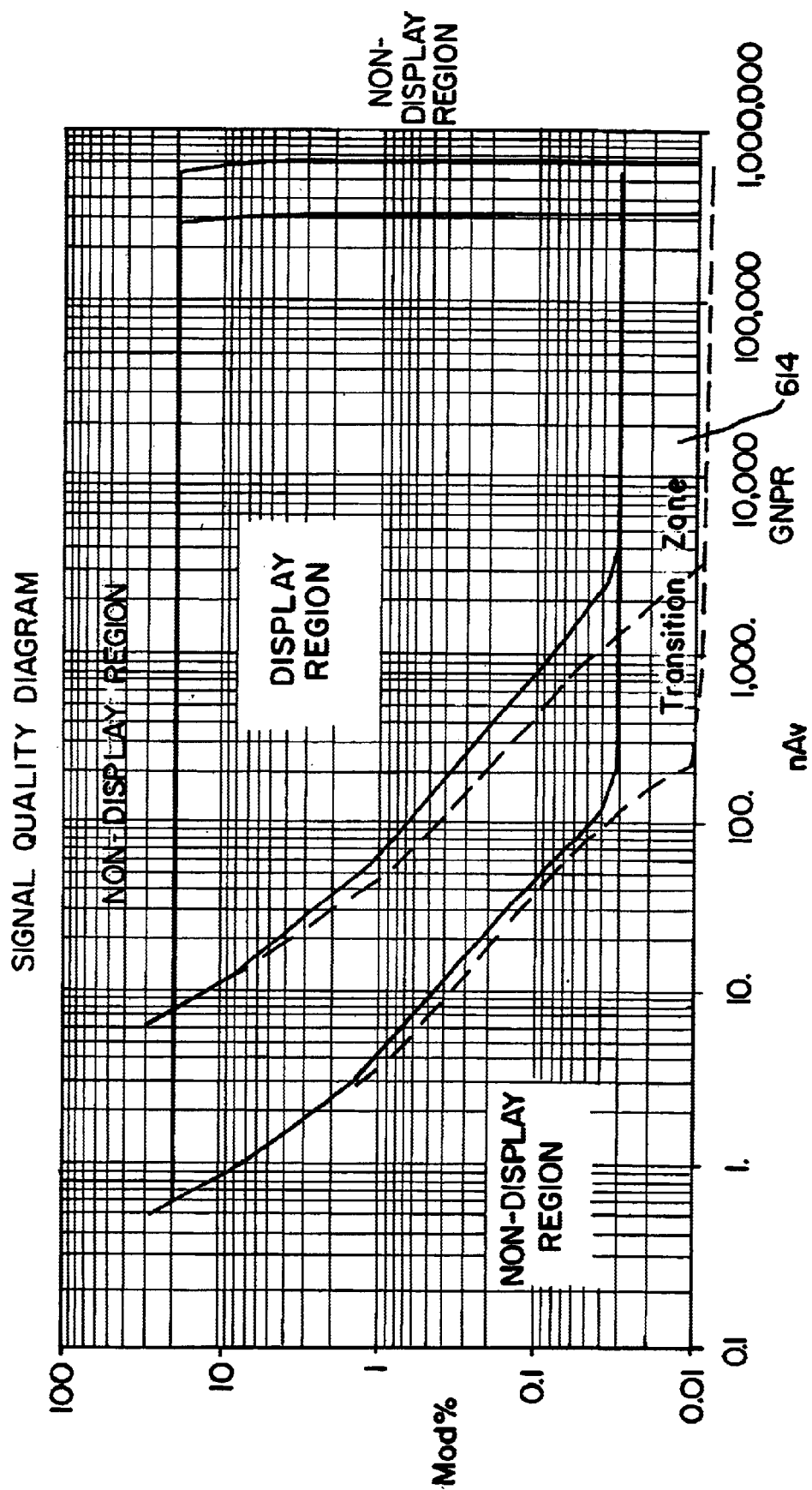
FIG. 6 shows a signal quality diagram having defined display and non-display regions (similar to those of FIG. 5) and transition zones.

FIG. 6 shows a signal quality diagram having defined display and non-display regions (similar to those of FIG. 5) and a transition zone 614. Transition zone 614 includes regions of the diagram that lie between the display and non-display regions. The transition zone represents regions associated with a different (e.g., intermediate) quality and accuracy level than those of the display and non-display regions. A different set of criteria can be used when evaluating data points that fall within the transition zone, as described below.

The regions shown in FIGS. 5 and 6 are only representatives of a particular oximeter/sensor combination and for a particular set of operating conditions. Each oximeter (or each oximeter model or type) is typically associated with its own set of display and non-display regions, which may differ from those shown in FIGS. 5 and 6. Some oximeters may even have poorly defined non-display regions, where the boundaries vary depending on a set of factors. These factors include the signal-to-noise ratio (SNR) of the oximeter, the amount of ambient light, the wavelength of the sensor LEDs, and so on.

In an embodiment, the oximeter operates in accordance with the following set of rules:

- If both data points (i.e., for the red and infrared signals) fall within their respective display regions, the oximeter posts the result (e.g., the saturation estimate, and heart rate).
- If either data point falls within its non-display region, the oximeter does not post the result.
- In all other cases, the oximeter may or may not post the result. These cases include instances in which one of the signals falls in the transition zone and neither signal falls in the non-display region.

Thus, the saturation estimate is posted if the modulation percentage (Mod %) and the light level (DC components) for both the red and infrared wavelengths fall within the bounded areas of their respective display regions. In an embodiment, if the red signal falls within the red non-display region or if the infrared signal falls within the infrared non-display region, or both, then the oximeter does not post the saturation estimate. It can be noted that other sets of rules can also be applied. For example, in another embodiment, the result is posted if one of the data points falls within its display region and the other data point falls within the transition zone. In yet another embodiment, the oximeter posts the saturation estimate and also indicates either the regions in which the data points fall or a confidence level based on the regions in which the data points fall.

For clarity, FIG. 5 shows only display and non-display regions. These regions correspond to data points that are to be displayed and not displayed. However, additional regions can be defined within the signal quality diagram, with the additional regions corresponding to different confidence levels in the saturation estimate. Generally, the confidence level is high for data points that fall near the center of the diagram and decreases as the data points move away from the center. For the embodiment having multiple confidence levels, the oximeter can display the saturation estimate along with the confidence level.

For example, an "inactive" region can be defined and used to indicate when a sensor is not applied to a patient. The inactive region may be used to detect and notify when the sensor has been removed (i.e., fallen off) the patient. The inactive region lies outside the display and transition regions, correlates to measurements from sensors that are not attached to patients, and typically comprises a portion of the non-display region. This region can be defined through simulation or through empirical measurements. The oximeter computes the data points in the manner described above. If the data points fall inside the inactive region, the oximeter displays an indication that the sensor has been removed from the patient.

Figure 7:
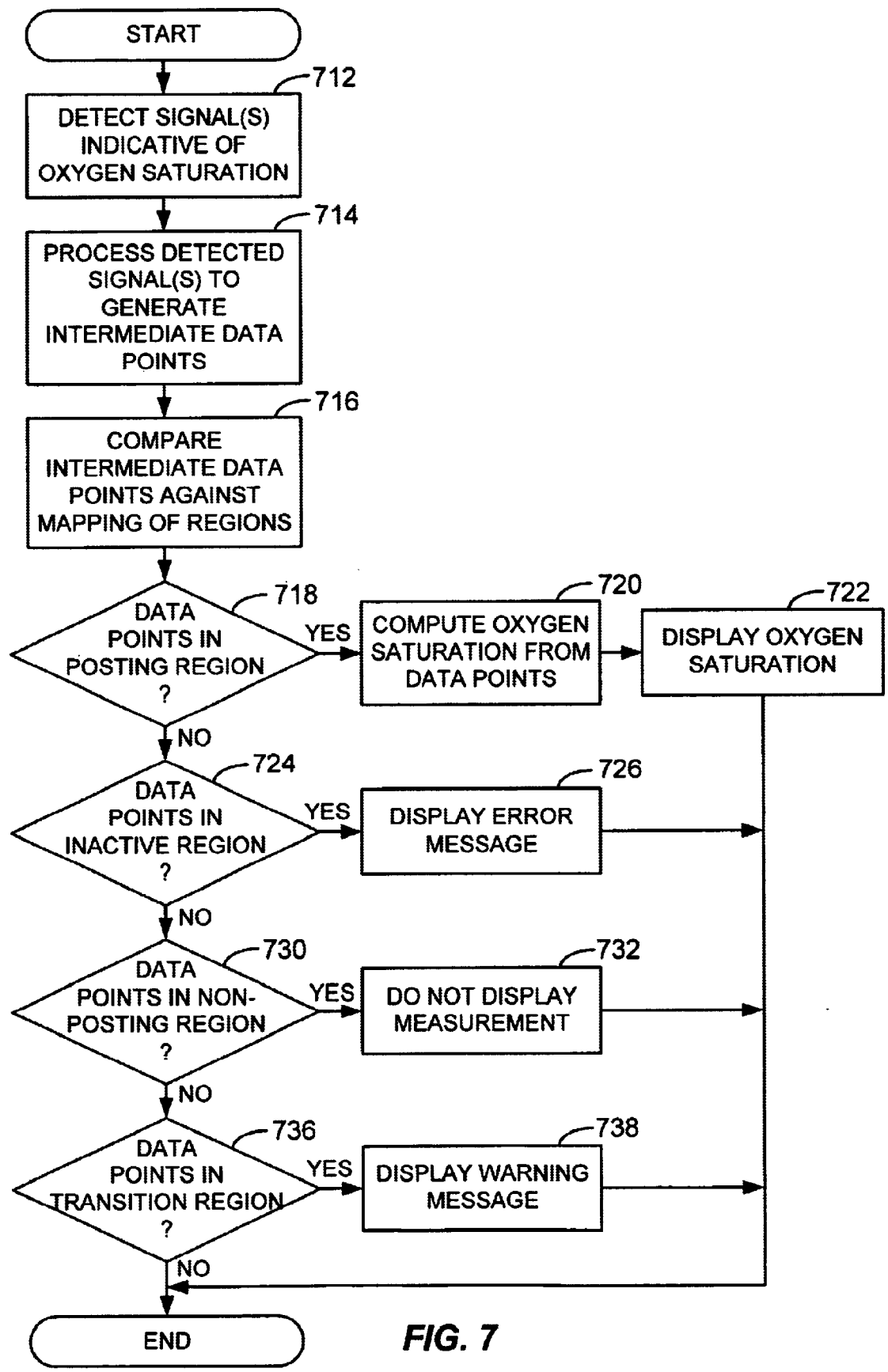
FIG. 7 shows a flow diagram of an embodiment of the measurement posting process of the invention.

FIG. 7 shows a flow diagram of an embodiment of the measurement display process of the invention. At a step 712, one or more signals indicative of a physiological parameter are detected. For an oximeter used to measure oxygen saturation, this detecting step may include, for example, receiving optical signals from two LEDs and conditioning these signals. At a step 714, the detected signal(s) are processed to generate intermediate data points. For oxygen saturation, this processing step may include filtering the data samples to generate DC and AC components, and using these components to generate the modulation percentage (Mod %). The intermediate data points would include filtered values for the DC component and computed values of the modulation percentage. The intermediate data points are then compared against a signal quality diagram (step 716). This diagram is generated previously, in a manner described above.

At step 718, it is determined whether the intermediate data points fall within the display region. If the answer is yes, the physiological parameter is estimated based on the detected and processed signal(s). For example, the oxygen saturation can be estimated from the computed Mod % for the two LEDs using equation (5). At step 722, the estimated physiological parameter is displayed, and the process terminates.

If it is determined at step 718 that the data points do not fall within the display region, a determination is made whether the data points fall within the inactive region (step 724). If the answer is yes, an error message is displayed at step 726. This error message may inform the clinician of the error data points (e.g., "ERROR MEASUREMENT"), provide a suggestion (e.g., "TRY ANOTHER SITE"), and so on. The process then terminates. In some embodiments of the invention, step 724 is not performed.

If it is determined at step 724 that the data points do not fall within the inactive region, a determination is made whether the data points fall within the non-display region, at a step 730. If the answer is yes, the measurement is not displayed. An error message may be displayed to inform the clinician. This error message may inform the clinician of the invalid data points (e.g., "INVALID MEASUREMENT" or "WEAK SIGNAL"), provide a suggestion (e.g., "TRY ANOTHER SITE"), and so on. The process then terminates.

If it is determined at step 730 that the data points do not fall within the non-display region, a determination is made whether the data points fall within the transition region, at step 736. If the answer is yes, a warning message may be displayed to warn the clinician. This warning message may indicate that the data points are of questionable accuracy (e.g., "INACCURATE MEASUREMENT" or "WEAK SIGNAL"), provide a suggestion (e.g., "TRY ANOTHER SITE"), and so on. The physiological parameter may also be computed and displayed along with the warning message. The process then terminates. In some embodiments of the invention, step 736 is not performed.

Figure 8:
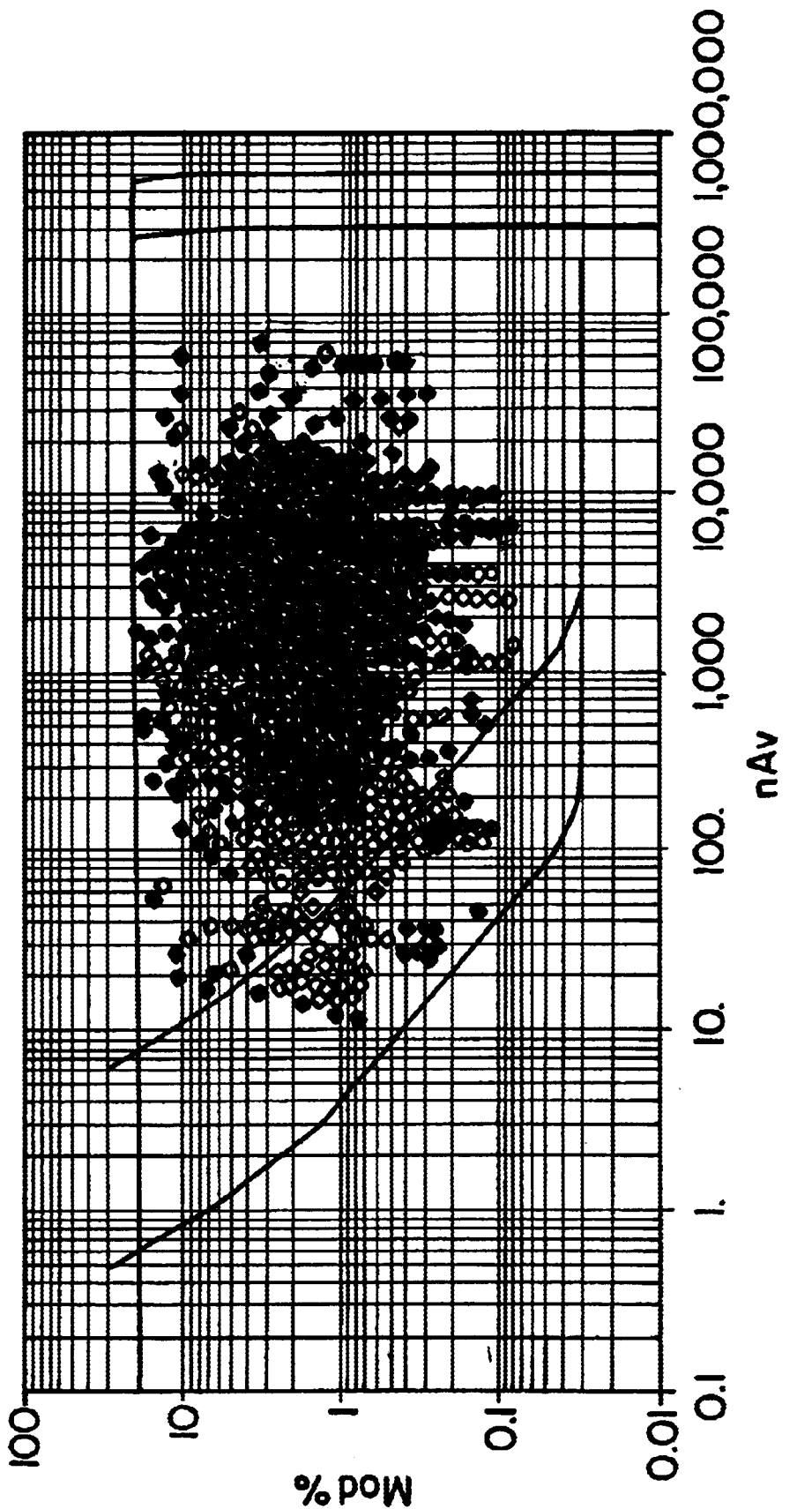
FIG. 8 shows a signal quality diagram with data collected from a patient population.

FIG. 8 shows a signal quality diagram with data collected from a patient population. The patient data can be used to define the display and non-display regions, to characterize the patient population's mean modulation percentage and mean nAv for both red and infrared wavelengths, to characterize measurement ambiguity that is indicative of the instrument's accuracy, or a combination of the above. Ambiguity as used herein, which is an approximate indication of instrument error, is the sum of the mean error (bias) of an instrument and the stability of the readings obtained (wander). The stability of the readings obtained (wander) is the standard deviation of the instrument readings.

The ambiguity, or estimated error, for various combinations of modulation and DC component are then plotted on the signal quality diagram. The average saturation, saturation bias, saturation wander, and ambiguity can be computed using equal weighting (i.e., giving the same importance for each data point) or unequal weighting that accounts for population statistics (i.e., giving less importance to data points that occur more rarely). Signal specification boundaries can also be obtained for a particular patient sub-population (e.g., perinatal patients) to further improve accuracy in the measurement reporting when the instrument is used for that particular patient sub-population.

Figure 9:
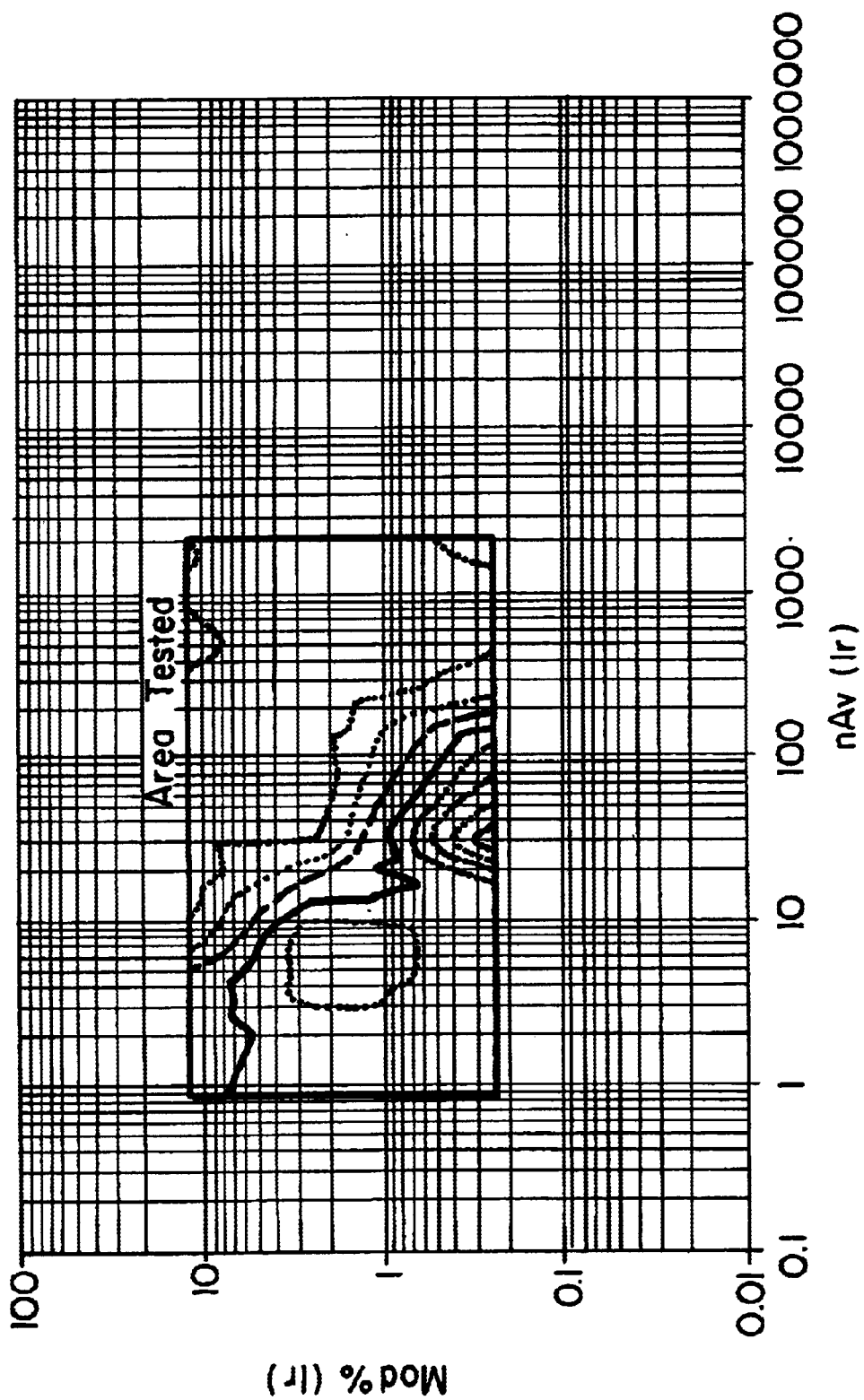
FIG. 9 shows a signal quality diagram that includes ambiguity contours plotted over a portion of the display region.

FIG. 9 shows a signal quality diagram that includes ambiguity contours plotted over a portion of the display region. Each contour line corresponds to a particular ambiguity, in saturation points. As an example, at an infrared operating point of 10 nAv and three percent modulation, the plots show an ambiguity of between 10 and 12 saturation points. The contour lines can be generated by collecting data points, grouping the data points that have similar infrared DC components, and selecting a representative ambiguity for those data points. The selected ambiguities for the groups of data points are plotted as a two-dimensional contour plot.

In an embodiment, the largest ambiguity in each group is selected as representative of the group and a contour plot of the worse case ambiguity is generated. This information is useful, for example, in an oximeter having a guaranteed limit on the saturation ambiguity, and only data points within the guaranteed limit are posted. Other variations of the contour plots shown in FIG. 9 are possible. For example, contour plots can be generated for: (1) the worst case ambiguity, (2) the average ambiguity, (3) the worst case or average absolute value of the bias, (4) the worst case or average value of the wander, and others. The average ambiguity contour plots are generated based on the average of the ambiguities obtained for each group, and are useful for indicating typical ambiguity that is likely to occur for that modulation and infrared DC component.

The contour plots on the signal quality diagram can also be adjusted for, or take into account, different pulse rates and abnormal heart rhythms such as arrhythmias, premature ventricular contractions, bigeminy, fibrillation, cardiac arrest, and other cardiac pathologies.

The invention provides advantages not available in conventional oximeters. For example, by detecting data points corresponding to saturation estimates having a low degree of confidence and discarding these estimates (or indicating the low degree of confidence), the invention provides an oximeter having improved diagnostic accuracy and reliability. This ensures that the results relied upon by the clinician meet a predetermined reliability criteria. The invention may also be used to detect and notify when the sensor has been removed (i.e., fallen off) the patient, as described above.

The oximeter of the invention can also be used to assist the clinician take more accurate measurements. This is a particularly useful application of the invention since it is known that some clinicians move the sensor to various parts of the patient in an attempt to obtain better readings. To assist the clinician, the oximeter can be programmed to display an indicator signal that indicates whether a selected site is good or poor for application of the sensor. This prompt may also be used to assist a less experienced clinician administer the saturation measurement.

The invention can be used for various physiological measurements. The application of the invention to pulse oximetry has been described as only one preferred embodiment. The invention can also be applied to other physiological measurements such as ECG, blood pressure, temperature, heart rate, and so on. Accordingly, the invention is not to be limited for use only with oximetry or pulse oximetry The foregoing description of the preferred embodiments is provided to enable any person skilled in the art to make or use the present invention. Various modifications to these embodiments will be readily apparent to those skilled in the art, and the generic principles defined herein may be applied to other embodiments without the use of further invention. For example, the invention can be applied to measurements of other physiological characteristics. Thus, the present invention is not intended to be limited to the embodiments shown herein but is to be accorded the widest scope consistent with the principles and novel features disclosed herein.

What is claimed is:

1. A system comprising a sensor and a monitor for sensing at least one physiological characteristic of a patient, the sensor being connectable to a monitor that estimates a physiological characteristic from signals detected by the sensor, the sensor comprising:

a detector for detecting the signals from the patient which are indicative of the physiological characteristic;

a memory connected with the sensor, said memory being physically located on one of a sensor body, sensor cable, sensor connecting plug or a sensor adapter module, and said memory being configured to store data defining at least one sensor signal specification boundary for the detected signals, the sensor signal specification boundary being indicative of a quality of the signals and an accuracy of the physiological characteristic estimated from the signals by the monitor; and means for providing access to the memory to allow transmission of the data defining the at least one sensor boundary to the monitor, wherein the monitor determines to display or not display the estimate of the physiological characteristic based on the signals and their relationship relative to a plurality of sensor signal specification boundaries and to a plurality of monitor boundaries preprogrammed into the monitor.

2. The system of claim 1, wherein the sensor signal specification boundary includes limits for an AC modulation component of the signals.

3. The system of claim 1, wherein the sensor signal specification boundary includes limits for a DC component of the signals.

4. The system of claim 1, wherein the monitor computes calculated values, having AC and DC components, from the signals, wherein the sensor signal specification boundary constitutes limits on the AC and DC components of the calculated values, and wherein the AC and DC components are dependent on either a physiological status of the patient, sensor type, or sensor location.

5. The system of claim 1, wherein the signals detected from the patient include first and second sets of signals derived from detected light scattered from the patient, the light having first and second wavelengths, the signals derived from detected light each having an AC modulation component and a DC component, and the sensor signal specification boundary including limits on the AC and DC components.

6. The system of claim 5, wherein the signals derived from detected light are indicative of an arterial oxygen saturation of the patient.

7. The system of claim 1, wherein the memory comprises a digital memory configured to store a digital representation of the at least one sensor signal specification boundary, and wherein the physiological characteristic is arterial oxygen saturation.

8. A system comprising a sensor and a monitor for sensing at least one physiological characteristic of a patient, the sensor being connectable to a monitor that estimates a physiological characteristic from signals detected by the sensor, the sensor comprising:

a detector for detecting the signals from the patient which are indicative of the physiological characteristic;

a memory connected with the sensor, said memory being physically located on one of a sensor body, sensor cable, sensor connecting plug or a sensor adapter module, and said memory being configured to store data defining at least one sensor signal specification boundary for the detected signals, the sensor signal specification boundary being indicative of a quality of the signals and an accuracy of the physiological characteristic estimated from the signals by the monitor; and means for providing access to the memory to allow transmission of the data defining the at least one sensor boundary to the monitor, wherein the monitor displays an indication of the quality of the signals based on their relationship relative to a plurality of sensor signal specification boundaries and to a plurality of monitor boundaries preprogrammed into the monitor.

9. A monitor for providing an indication of an accuracy of an estimated physiological condition of a patient, the monitor being connectable to a sensor that detects signals indicative of at least one physiological characteristic of the patient, the monitor comprising:

at least one receiving circuit configured to receive the signals indicative of the at least one physiological characteristic from the sensor and data defining at least one sensor signal specification boundary for the detected signals from the sensor, the sensor signal specification boundary being indicative of a quality of the signals detected by the sensor and an accuracy of the physiological characteristic estimated from the detected signals;

at least one processing circuit configured to estimate the physiological condition of the patient based on the received signals, compare the received signals against the at least one sensor boundary, and generate the indication of the accuracy of the estimated physiological condition; and means for providing the indication of the accuracy of the estimated physiological condition to a user of the monitor, wherein said processing circuit determines to display or not display the estimate of the physiological characteristic based on the signals and their relationship relative to a plurality of sensor signal specification boundaries and to a plurality of monitor boundaries preprogrammed into the monitor.

10. The monitor of claim 9, wherein the at least one sensor boundary is indicative of a transition between a signal regime considered normal for the sensor in its usual application and a signal regime considered to be abnormal.

11. The monitor of claim 10, wherein the at least one processing circuit is further configured to determine whether the received signals are within the normal regime or the abnormal regime.

12. The monitor of claim 10, wherein the at least one processing circuit is further configured to compute an indication of whether the sensor is likely to be applied to the patient or has partially or entirely came off the patient.

13. A physiological monitoring system comprising:

a sensor that includes a detector for detecting signals from a patient which are indicative of at least one physiological characteristic of the patient;

a memory connected with the sensor, said memory being physically located on one of a sensor body, sensor cable, sensor connecting plug or a sensor adapter module, and said memory being configured to store data defining at least one sensor boundary for the detected signals; and a monitor coupled to the sensor and the memory, the monitor includes at least one receiving circuit configured to receive the detected signals and the data defining the at least one sensor boundary from said memory connected with said sensor, at least one processing circuit configured to estimate a physiological condition of the patient based on the received signals, compare the received signals against the at least one sensor boundary, and generate an indication of an accuracy of the estimated physiological condition, and means for providing the indication of the accuracy to a user of the system, wherein the monitor determines to display or not display the estimate of the physiological characteristic based on the signals and their relationship relative to a plurality of sensor boundaries and to a plurality of monitor boundaries preprogrammed into the monitor.

14. A system comprising a sensor and a monitor for sensing at least one physiological characteristic of a patient, the sensor being connectable to a monitor that estimates the physiological characteristic from signals detected by the sensor, the sensor comprising:

a detector for detecting the signals from the patient which are indicative of the physiological characteristic;

a memory connected with the sensor, said memory being physically located on one of a sensor body, sensor cable, sensor connecting plug or a sensor adapter module, and said memory being configured to store data defining at least one sensor signal specification boundary for the detected signals, the sensor signal specification boundary being indicative of a transition between a signal regime considered normal for the sensor in its usual application, and a signal regime considered to be abnormal; and means for providing access to the memory to allow transmission of the data defining the at least one sensor boundary to the monitor, wherein the monitor determines to display or not display the estimate of the physiological characteristic based on the signals and their relationship relative to a plurality of sensor signal specification boundaries and to a plurality of monitor boundaries preprogrammed into the monitor.

15. The system of claim 14, in which said sensor signal specification boundary is characteristic of a model of the sensor.

16. The system of claim 14, in which said boundary is characteristic of individual components used in making the sensor.

17. The system of claim 15:

wherein the monitor is a pulse oximetry monitor having means to determine whether the signals are within said normal regime or said abnormal regime; and means for informing a user of the system as to whether the signal is normal or abnormal.

18. The system of claim 17, wherein said means for informing the user is an alarm that is triggered when the signal moves from said normal regime to said abnormal regime.

19. The system of claim 17, wherein said normal regime is one in which the sensor is likely to be properly applied to the patient and said abnormal regime is one in which the sensor may have partially or entirely come off the patient.

20. A pulse oximetry system comprising:

a sensor for sensing at least one physiological characteristic of a patient, the sensor being connectable to a monitor that estimates the physiological characteristic from signals detected by the sensor, the sensor comprising a detector for detecting the signals from the patient which are indicative of the physiological characteristic;

a memory connected with the sensor, said memory being physically located on one of a sensor body, sensor cable, sensor connecting plug or a sensor adapter module, and said memory being configured to store data defining at least one sensor signal specification boundary for the detected signals, the sensor signal specification boundary being indicative of a transition between a signal regime considered normal for the sensor in its usual application, and a signal regime considered to be abnormal; and means for providing access to the memory to allow transmission of the data defining the at least one sensor boundary to the monitor, and the system further comprising a pulse oximetry monitor that includes means to determine whether the signals are within said normal regime or said abnormal regime, said normal regime being one in which the sensor is likely to be properly applied to the patient and said abnormal regime being one in which the sensor may have partially or entirely come off the patient, means to compute other measures which indicate a probability that the sensor has come off the patient, wherein said other measures include one of a signal-to-noise ratio, amount of ambient light present, sensor type and measurement ambiguity, and means to combine mathematically indication of whether the signals are within said normal regime or said abnormal regime and the other measures so as to compute a net probability that the sensor has come off the patient.

* * * * *